United States Patent
Kazatchkov et al.

(10) Patent No.: US 6,723,123 B1
(45) Date of Patent: Apr. 20, 2004

(54) PROSTHETIC HEART VALVE

(75) Inventors: Lev Kazatchkov, Mendoza (GB); Lucas Varela, Mendoza (GB)

(73) Assignee: Impsa International Incorporated, Pittsburgh, PA (US)

( * ) Notice: Subject to any disclaimer, the term of this patent is extended or adjusted under 35 U.S.C. 154(b) by 0 days.

(21) Appl. No.: 10/129,894
(22) PCT Filed: Nov. 10, 1999
(86) PCT No.: PCT/IB99/01816
§ 371 (c)(1), (2), (4) Date: Sep. 13, 2002
(87) PCT Pub. No.: WO01/34068
PCT Pub. Date: May 17, 2001

(51) Int. Cl.$^7$ .................................................. A61F 2/06
(52) U.S. Cl. ...................................... 623/2.2; 623/2.21
(58) Field of Search ................ 623/2.2–2.25, 623/2.26–2.3, 2.31–2.33

(56) References Cited

U.S. PATENT DOCUMENTS

| | | | |
|---|---|---|---|
| 3,312,237 A * | 4/1967 | Mon et al. ............. | 137/512.15 |
| 4,373,216 A * | 2/1983 | Klawitter ................ | 623/2.22 |
| 4,908,028 A | 3/1990 | Colon et al. ............... | 623/2 |
| 5,197,980 A | 3/1993 | Gorshkov et al. ......... | 623/2 |
| 5,607,469 A | 3/1997 | Frey ........................... | 623/2 |
| 6,638,303 B1 * | 10/2003 | Campbell ................ | 623/2.2 |

FOREIGN PATENT DOCUMENTS

GB 2281371 3/1995 .............. A61F/2/24

* cited by examiner

*Primary Examiner*—David H. Willse
*Assistant Examiner*—Hieu Phan
(74) *Attorney, Agent, or Firm*—Drinker Biddle & Reath LLP

(57) ABSTRACT

A multi-leaflet cardiovascular valve having a generally annular valve body (1) and at least two leaflets (4, 5) mounted within the valve body such that the leaflets rotate around a central axis (11) and a transverse pivoting axis (12) between an open configuration wherein blood is permitted to flow through the annular valve body and a closed configuration wherein blood is prevented from flowing in at least one direction through the annular valve body. During the open configuration, the leaflets rotate around the flow axis.

8 Claims, 4 Drawing Sheets

PROSTHETIC HEART VALVE

DESCRIPTION

The present invention relates to a cardiac valve prosthesis and more particularly refers to a mechanical cardiovascular valve of the type comprising a plurality of leaflets as means for closing and opening the valve.

It is well known in the cardiovascular medical technology to provide heart valve prothesis designed to replace defective and/or diseased natural cardiac valves. A cardiac valve must allow the blood flow to freely circulate there through when in an open position and must prevent blood back flow through the valve when the same is closed. These are basically the functions of a natural cardiac valve and the same objectives must be accomplished by any prosthetic heart valve. Many shortcomings and drawbacks of the several attempts made to obtain a heart valve prosthesis have caused to fail in providing a mechanical valve capable of resembling a natural heart valve and complying with the functions thereof. This is mainly due to the fact that the fluid under processing, the blood, is not a fluid like any other one, instead, the blood is a very delicate tissue that is able to be spoiled by even minor undue treatment caused, for instance, by turbulence and high shear stresses in the flow that can either produce thrombosis or emboli at local regions of stagnation, for example.

Several prosthetic heart valve mechanisms have been developed in an attempt to comply with the above remarked requirements without the mentioned drawbacks and failures. These valves typically are comprised of a valve body that accommodate valve members such as a single occluder or a plurality of occulders consisting of articulated or pivoting leaflets, for example. In other types of valves the occluder consists of a ball located in a cage, also known as ball-in-cage valves, wherein the ball is capable of seating against a seat of the valve body to close the pass through the valve, and moving away from the seat to open the valve. In some valves, members are provided that are capable of pivoting around fixed shafts or movable shafts, and some valves have been developed to have some freedom by altering the leaflet position relative to the central axis of the valve, always to improve the desired washing effect of such areas where the blood flow is zero and the blood remains stationary, also known as "dead areas".

U.S. Pat. No. 4,274,437 to Lens S. Watts discloses a heart valve prosthesis comprising leaflets that both pivot and gradually orbit about an axis of the valve thus eliminating localized wear which otherwise occur at the locations in the valve body against which the rotating pivot would bear. It is not clearly disclosed, however, how the necessary forces are generated and applied to the leaflets for producing the orbiting about the axis of the valve. Moreover, leaflets do not open fully and there is no solution provided for eliminating turbulence and drag forces when the valve is open.

U.S. Pat. No. 5,197,980 to Jury V. Gorshkov discloses a cardiac valve prosthesis having valve members that open and close freely and rotate simultaneously around the body axis. The object of this invention is to produce additional back swirling of the blood flows forcing the valve members to rotate about the body axis and to intensively flush the prosthesis components by means of forward and reverse blood flows, thereby effectively improving the resistance to a thrombus formation. Again, this valve does not open in a fully mode to provide complete pass to the blood and does not provide a solution to the prevention of turbulence and drag forces when the valve is open.

U.S. Pat. No. 5,861,029 to Sergey Evdokimov discloses a heart valve prosthesis having leaflets with an additional degree of freedom, wherein the leaflets have the possibility of rotating around a central axis of an annular body. The problem underlying the invention is to create a heart valve prosthesis comprising a hinge mechanism that holds the leaflets within the valve body. This patent attempts to prevent thrombus formation by eliminating localized stagnation zones inaccessible to blood washing, and improve the hemodynamic characteristics of the valve prosthesis and extend its lifetime. This valve does not provide a full opening thereof and does not provide a solution to the turbulence and drag forces when the valve is open.

It is well known that the key of a hemodynamic flow in a natural valve is the ability to produce non turbulent flow. Natural valves open fully to provide a complete section pass and offer little or no resistance to the flowing fluid. There are no dead areas wherein blood flow stagnates and may coagulate. Further, there are no areas of turbulent flow that can damage the red blood cells and the platelets.

Unfortunately, the prior art valves still suffer from dead areas and turbulent flow. In the fully open position leaflets form an angle with the flow to assure proper closing of the valve upon dropping of the blood pressure and reversing of the blood flow during the diastolic movement of the cardiac cycle. Alternatively, the leaflets may hang parallel to the blood flow in the open position but with their downstream edges curved slightly to favour closing during diastolic cycle.

The dilemma is that a rapid valve closure has been obtained till now at the price of more turbulence and drag forces.

It is therefore an object of the present invention to provide a mechanical valve with minimal or no turbulence and minimal or no drag forces generated in the open position of the valve during the systolic pulse of the heart cycle.

It is still another object of the present invention to provide a mechanical heart valve having at least two leaflets rotating around a central axis of an annular body of the valve when the valve is not in a closed position.

Accordingly, the present invention provides a prosthetic heart valve comprising an annular body having an inner surface and an outer surface and defining a central axis of the annular body, at least two leaflets pivotally mounted to said annular body, the leaflets including pivoting means connecting the leaflets together and to the inner surface of the annular body, the pivoting means defining a pivoting axis dividing each leaflet in two sectors, one sector larger than the other, whereby the blood flow impinging onto the larger sector of each leaflet causes the leaflet to pivot around the pivoting axis and rotate around the central axis so as to define a uniform and axial flow in the blood passing through the valve.

It has been found that leaflets rotating around the central axis of the annular body are effective to eliminate the turbulent flow and drag forces when the valve is not in the closed position.

Preferably, the pivoting axis extends normally to the central axis.

The pivoting means may also comprise a central axis shaft connected to the annular body, a rotary sleeve freely mounted around the central shaft, the sleeve having radially extending pins, and each leaflet being rotatably mounted to each pin whereby each pin defines the pivoting axis for the associated leaflet.

The above and other objects, features and advantages of the present invention will be better understood when taken in connection with the accompanying drawings and description.

The present invention will now be illustrated by way of example only to the accompanying drawings in which.

Figure 1:
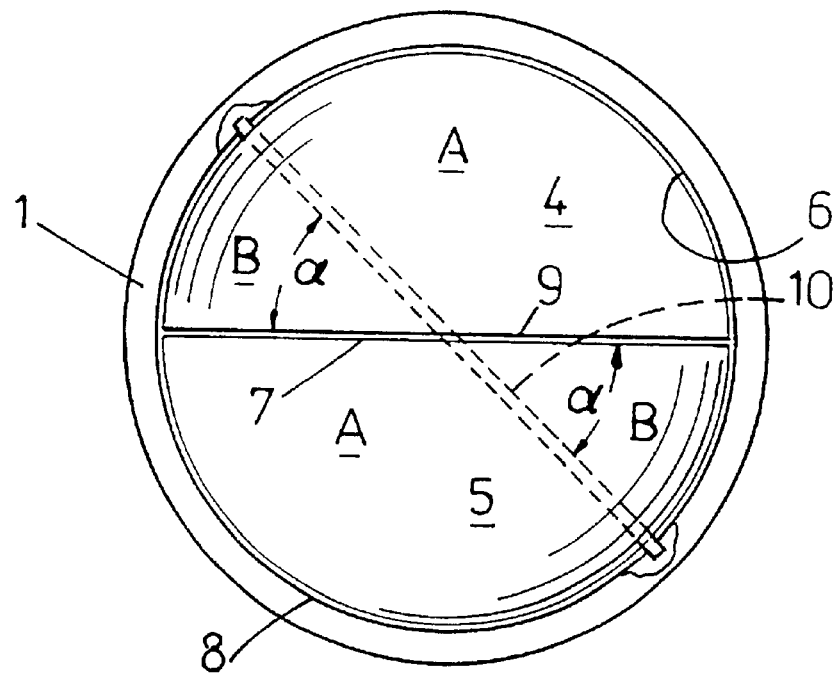
FIG. 1 is a top plan view of a heart bi-leaflet valve in accordance with the present invention, shown in the closed position.
Figure 2:
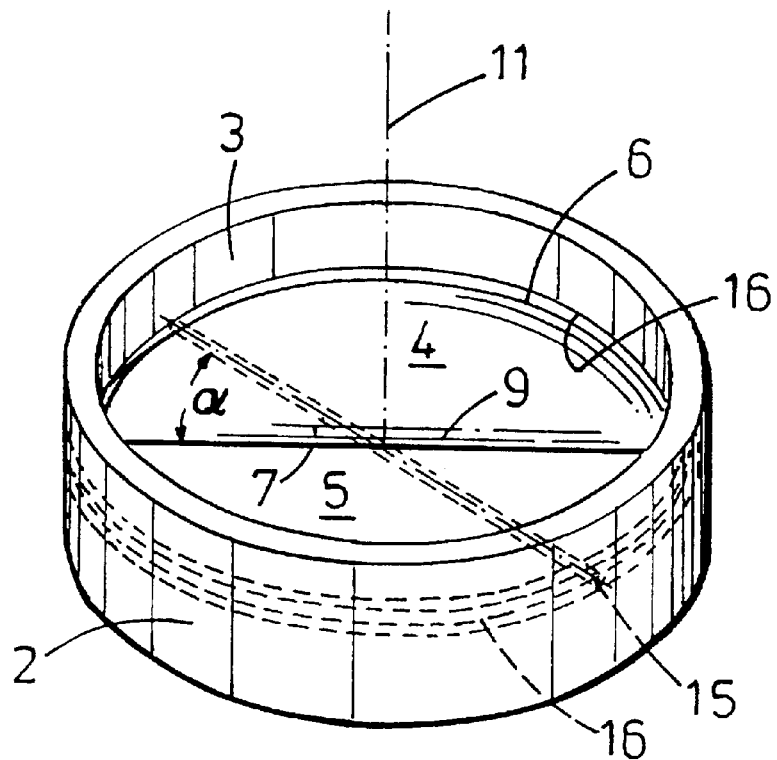
FIG. 2 is a perspective top view of the bi-leaflet valve of FIG. 1, shown in the closed position.

Now referring in detail to the drawings it may be seen from FIGS. 1, 2 a heart valve according to the invention comprising an outer annular body 1, preferably an axis-symmetrical body and more preferably a cylindrical body defining an outer surface 2 and an inner surface 3, housing two leaflets 4, 5 pivotally mounted in body 1, preferably on inner surface 3. Each leaflet 4, 5 has a semi-circular shape with a circular periphery 6, 8 and an inner edge 7, 9 with the inner edges of the leaflets abutting each other to perfectly close the pass through the valve when the valve is, as illustrated in FIGS. 1 and 2, in the closed position. Leaflets 4, 5 are pivotally connected to each other and to body 1 by means of pivoting mens comprising a pivoting axis shown in phantom lines and indicated by reference number 10. Annular body 1 defines a central axis 11 passing by the centre of the cylindrical body and the intersection of edges 7, 9 and pivoting axis 10.

Axis 10 may comprise a pivoting shaft 12 extending through the leaflets, passing along respective orifices 13 (see FIG. 5) formed in the leaflets. Shaft 12 may comprise any kind of rod or wire made of a proper medical material, such as a metal. Shaft 12 may comprise a continuous elongated piece extending along the entire diameter of the valve or may comprise separate pieces each one extending in the corresponding leaflet. In any event it is convenient that shaft 12 has opposite ends 14, 15 protruding from the peripheral edges 6, 8 of the leaflets, the ends 14, 15 defining a pivoting mounting in the inner surface 3 of the body 1, preferably ends 14, 15 will be freely housed in a continuous groove 16 formed in inner surface 3, whereby shaft 12 may move along the entire circumference of the groove.

Figure 3:
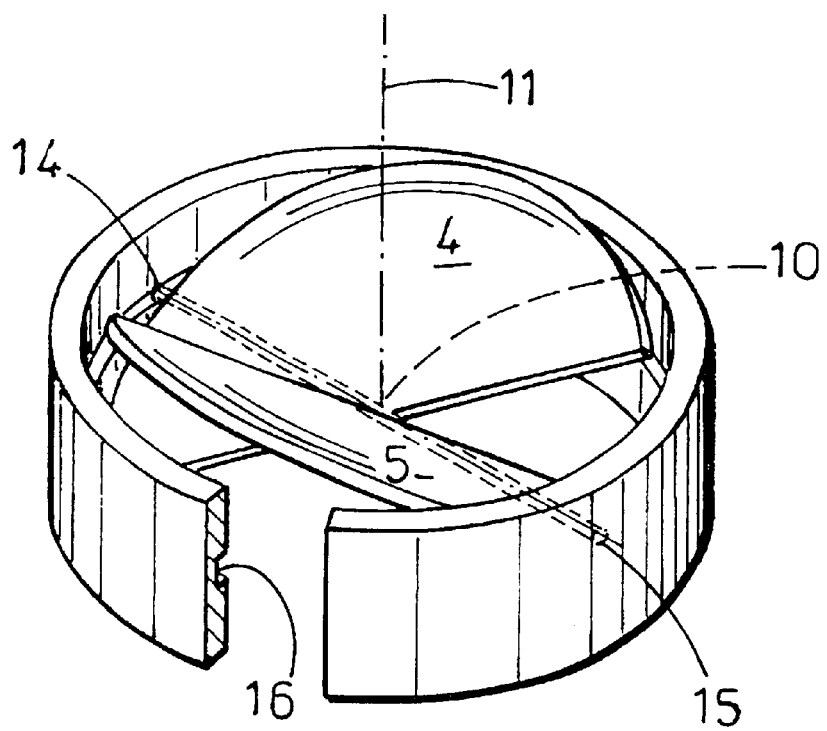
FIG. 3 is a top perspective, partially cross-sectioned, view of the valve in accordance with the present invention, shown in an open position.
Figure 4:
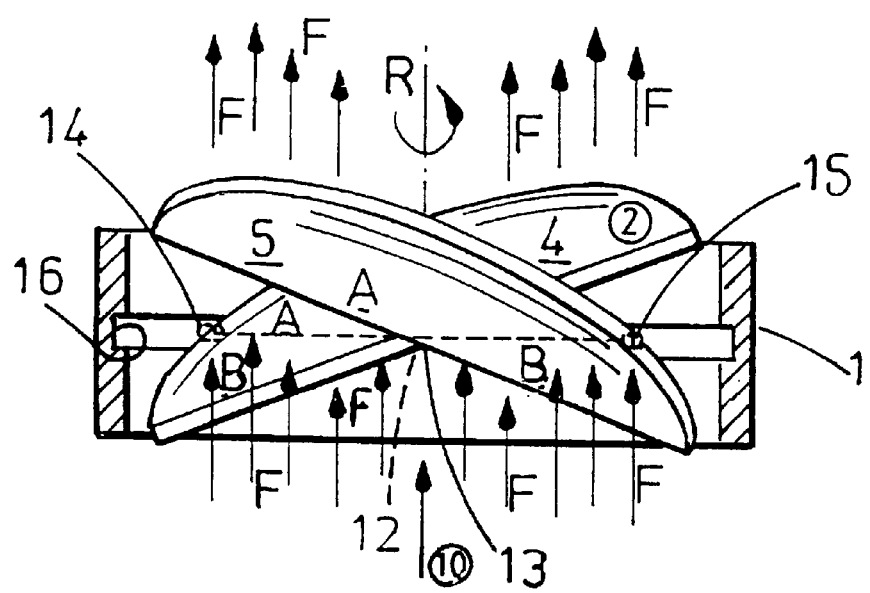
FIG. 4 is a side diametrical cross-section view taken along a plane, perpendicular to a common pivoting axis of the leaflets, of the valve in accordance with the present invention, shown in the open position.
Figure 5:
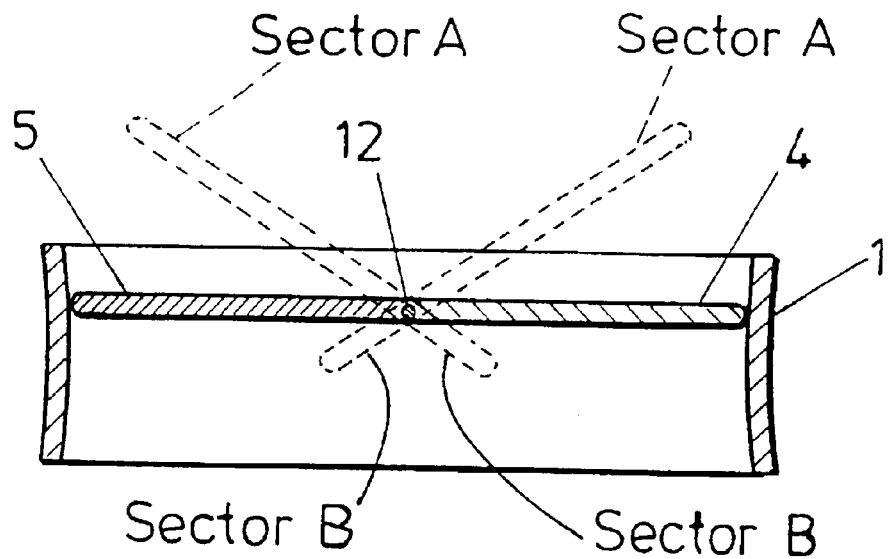
FIG. 5 is a side partial cross-section view of the valve of the present invention, shown in the open position.

Pivoting axis 10 crosses edges 7, 9 of the leaflets forming an acute angle a whereby each leaflet is divided into two sectors, one sector A being larger than the other sector B. Therefore, when the valve is fixed to a blood vessel the blood flow, indicated by arrow F in FIG. 5, impinging onto the leaflets will generate on larger sectors A respective forces larger than the forces resulting from the blood flow onto sectors B. This will result in that the hydraulic torque about axis 10 due to sectors A being larger than the hydraulic torque about axis 10 due to sectors B. This causes the leaflets to pivot around the pivoting axis in a pattern as it is illustrated in FIGS. 3 to 5, with the larger sectors A moving in the sense of the blood flow and sectors B rotating against the blood flow. Under these circumstances, the leaflets behave like a fan under the wind action, or a propeller, thus rotating around central axis 11, as indicated by arrow R in FIG. 5, whereby the leaflets define a rotation in a pattern to define an axial and uniform flow in the blood passing through the valve, as indicated by arrows F. The rotation and opening movement velocity of the leaflets will be inversely proportional to the value of angle α. FIG. 4 shows a diametrical section taken along a plane perpendicularly passing through the shaft 12 to illustrate the opening pattern of the leaflets.

Figure 6:
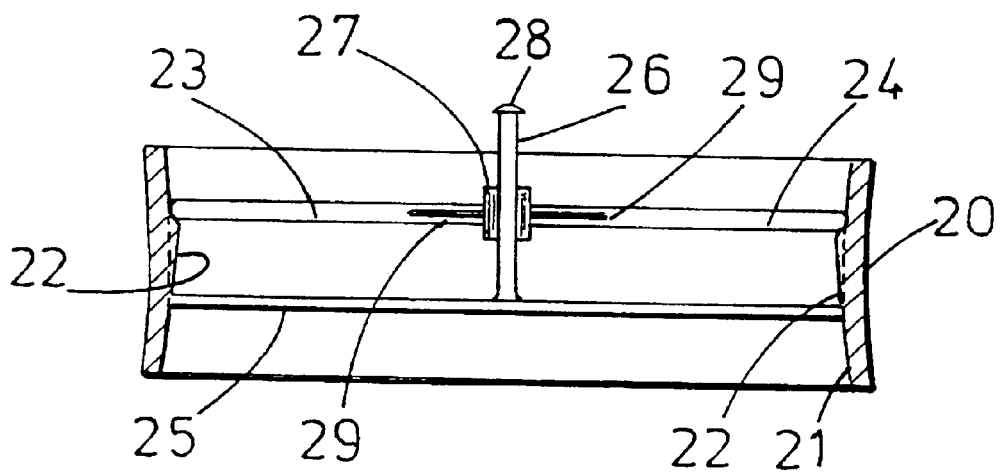
FIG. 6 is a side diametric cross-section view of a valve in accordance with an alternative embodiment of the present invention, shown in the closed position.

FIG. 6 shows another embodiment of the present invention wherein the valve comprises an annular body 20 defining an inner surface 21 including a continuous shoulder 22 forming a closing seat for leaflets 23, 24 which are similar to the leaflets shown in FIGS. 1 to 5 but differing therefrom in the mounting of the leaflets on the body. According to this embodiment, a support 25 is fixed to body 20 and a central axis shaft 26 is provided at a central portion of support 25. A sleeve 27 is freely mounted on shaft 26 and is free to rotate around shaft 26 and axially move along shaft 26 up to a stop 28. Sleeve 27 has two or more pins 29 radially extending from the sleeve. Pins 29 may be connected to a sleeve 27 in a way that can rotate relative to the sleeve or may be fixed to the sleeve. In the latter case where the pins are firmly fixed to the sleeve, each pin will be inserted into a respective leaflet 23, 24 in such a way that the associated leaflet is capable of rotation around pin 29, thus each pin defining the pivoting axis for the associated leaflet.

Figure 7:
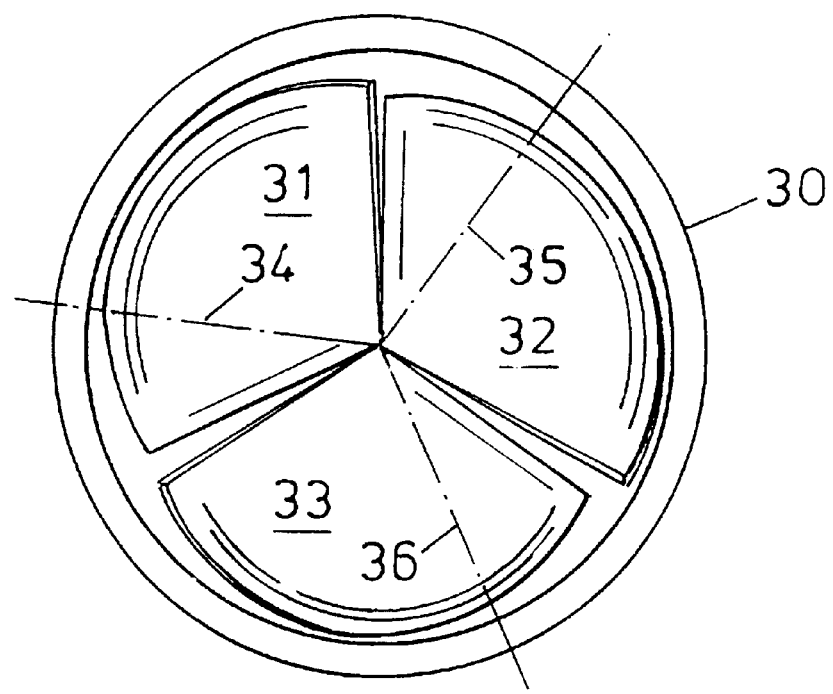
FIG. 7 and FIG. 8 are respective top plan views of alternative embodiments of the present invention with three and four leaflets, shown in the open position.

FIG. 7 shows another alternative of the valve of the invention, showing a valve body 30 comprising three leaflets 31, 32, 33 pivotally mounted in associated pivoting axis 34, 35, 36 by means of any of the above described and mentioned pivoting and mounting means.

Figure 8:
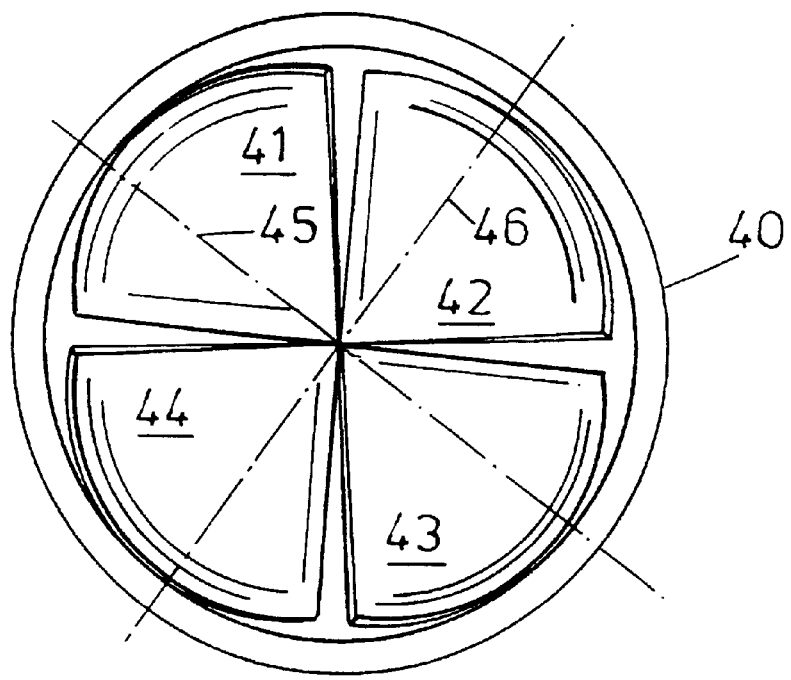

FIG. 8 shows another alternative of the valve of the invention, showing a valve body 40 comprising four leaflets 41, 42, 43, 44 pivotally mounted in associated pivoting axis 45, 46, by means of any of the above described and mentioned pivoting and mounting means.

According to the invention, it has been found that when the valve is in the open position blood flow pressure onto the leaflets produces a torque around central axis 11 that causes the leaflets to rotate as shown in FIG. 5, when the blood flow circulates in an axial and uniform pattern, as it is also shown in the drawings (FIG. 5).

The angular velocity of the leaflets around the central axis 11 is inversely proportional to the opening angle of the leaflets.

The continuous fluid flow behaviour through a valve with leaflets rotating around the central axis of the valve body is mathematically defined by the Euler equation. According to Euler, the torque on leaflets 4 and 5 due to the hydraulic forces is proportional to the variation of the tangential component of the fluid velocity. The Euler equation is:

$$(R \cdot C_u)_1 - (R \cdot C_u) = \frac{\eta g \cdot H}{\omega}$$

where, $\Omega$=angular speed of the leaflets;
R=radius of a flow surface;
$C_u$=tangential component of absolute velocity;
H=pressure drop;

g=acceleration due to gravity;
η=efficiency;
index 1 is used for the valve inlet;
index 2 is used for the valve outlet;
The torque M on the leaflets is:

$$M = \frac{\eta g \cdot H \rho Q}{\omega}$$

where
ρ=blood specification mass
Q=flow discharge
If the Euler equation is multiplied by ρQ, then:

$$\rho Q[(R \cdot C_u)_1 - (R \cdot C_u)_2] = \frac{\eta g \cdot H \rho Q}{\omega}$$

Or $$\rho Q[(R, C_u)_1 - (R, C_u)_2] = M$$

Since the tangential component of the blood flow at the valve inlet is 0 (zero), and the torque on the leaflets is 0 (zero), when the leaflets are rotating freely around the central axis, then:

$$(R, C_u)_1 = 0$$

$$M = 0$$

Therefore, the tangential component at the outlet must be 0 (zero).

$$(R, C_u)_2 = 0$$

This is to demonstrate that, thanks to the leaflets rotation the blood exits the valve without a tangential flow component, that is, the blood flow exiting the valve is not helical, but is uniform and axial.

Therefore, the fluid uniformly flows through the valve and the drag forces due to static prior art leaflets disappear. There is a decrease of pressure drop and a dramatic reduction of blood damage and blood clotting. Given that the leaflets rotate around the central axis of the valve, there are no dead areas where, like in the prior art, the blood would remain stationary, and the desired washing effect is continuous during the open mode of the valve.

The present invention provides a mechanical heart valve with rotating leaflets when the valve is not in the closed position.

While preferred embodiments of the present invention have been illustrated and described, it will be obvious to those skilled in the art that various changes and modifications may be made therein without departing from the scope of the invention as defined in the appended claims.

What is claimed is:

1. A prosthetic heart valve comprising:

an annular body having an inner surface and an outer surface and defining a central axis of the annular body, at least two leaflets pivotally mounted to said annular body, the leaflets including pivoting means connecting the leaflets together and to the inner surface of the annular body, the pivoting means defining a pivoting axis dividing each leaflet in two sectors, one sector larger than the other, whereby the blood flow impinging onto the larger sector of each leaflet causes the leaflet to pivot around the pivoting axis and rotate around the central axis so as to define an axial flow in the blood passing through the valve.

2. A prosthetic heart valve as claimed in claim 1, wherein the annular body is axis symmetrical body.

3. A prosthetic heart valve as claimed in claim 1 or claim 2, wherein the inner surface of the annular body defines a continuous guide groove extending along the entire circumference of the inner surface.

4. A prosthetic heart valve as claimed in any one of claims 1 to 3, wherein the pivoting means comprise a shaft extending along the pivoting axis, the shaft having opposite ends protruding from the periphery of the leaflets to define a pivoting mounting on the inner surface of the annular body.

5. A prosthetic heart valve as claimed in claim 4, wherein the shaft extends through a respective orifice extending through the leaflets, the shaft having opposite ends protruding from the periphery of the leaflets to define a pivoting mounting on the inner surface of the annular body.

6. A prosthetic heart valve as claimed in claim 4, wherein the opposite ends protruding from the periphery of the leaflets are housed into the guide groove for defining the pivoting mounting of the shaft along the groove in the inner surface of the annual body.

7. A prosthetic heart valve as claimed in claim 1, wherein the opposite ends protruding from the periphery of the leaflets are housed into the guide groove for defining the pivoting mounting of the shaft along the groove in the inner surface of the annular body.

8. A prosthetic heart valve as claimed in claim 1, wherein the pivoting axis extends normally to the central axis.

* * * * *